US011672549B2

(12) United States Patent
Cundiff et al.

(10) Patent No.: US 11,672,549 B2
(45) Date of Patent: Jun. 13, 2023

(54) SURGICAL JIG

(71) Applicant: Fusion Orthopedics USA, LLC, Mesa, AZ (US)

(72) Inventors: Adam J. Cundiff, Gilbert, AZ (US); Nathan G. Peterson, Gilbert, AZ (US); Kolby K. Black, Spanish Fork, UT (US); Mark William Roberts, Jr., Gilbert, AZ (US); Scott Maling, Awatukee, AZ (US); Jason Harrill, Chandler, AZ (US)

( * ) Notice: Subject to any disclaimer, the term of this patent is extended or adjusted under 35 U.S.C. 154(b) by 291 days.

(21) Appl. No.: 17/182,131

(22) Filed: Feb. 22, 2021

(65) Prior Publication Data

US 2022/0151644 A1    May 19, 2022

Related U.S. Application Data

(60) Provisional application No. 63/115,201, filed on Nov. 18, 2020.

(51) Int. Cl.
| | |
|---|---|
| *A61B 17/17* | (2006.01) |
| *A61B 17/02* | (2006.01) |
| *A61B 17/84* | (2006.01) |
| *A61B 17/56* | (2006.01) |

(52) U.S. Cl.
CPC ........ *A61B 17/1775* (2016.11); *A61B 17/025* (2013.01); *A61B 17/842* (2013.01); *A61B 2017/565* (2013.01)

(58) Field of Classification Search
CPC ....... A61B 17/025; A61B 17/66; A61B 17/58; A61B 17/60; A61B 2017/603; A61B 17/64; A61B 17/6466; A61B 2017/0256; A61B 2017/0268; A61B 2017/0275; A61B 17/1775; A61B 2017/565
See application file for complete search history.

(56) References Cited

U.S. PATENT DOCUMENTS

| | | |
|---|---|---|
| D695,402 S | 12/2013 | Dacosta et al. |
| 9,622,805 B2 | 4/2017 | Santrock et al. |
| 9,687,250 B2 | 6/2017 | Dayton et al. |
| 9,936,994 B2 | 4/2018 | Smith et al. |
| 10,045,807 B2 | 8/2018 | Santrock et al. |
| 10,335,220 B2 | 7/2019 | Smith |
| 10,342,590 B2 | 7/2019 | Bays et al. |
| 10,512,470 B1 | 12/2019 | Bays et al. |
| 10,524,808 B1 | 1/2020 | Hissong et al. |
| 10,555,757 B2 | 2/2020 | Dayton |
| 10,561,426 B1 | 2/2020 | Dayton et al. |

(Continued)

*Primary Examiner* — Samuel S Hanna (57) ABSTRACT

Surgical jigs for use in an osteotomy are provided herein. One surgical jig includes a rail body, a contact coupled to the rail body and configured to engage a metatarsal of a subject, and an attachment body coupled to the rail body and configured to engage a cuneiform of the subject. Other surgical jigs include a rail body, a contact coupled to the rail body and configured to engage a metatarsal of a subject; an arm coupled to the rail body, an attachment body coupled to the arm and configured to engage a cuneiform of the subject, a rail hinge coupling the arm and the rail body, a rail adjustment screw coupled to the arm, a rotation guide coupled to the rail body, and a distraction body coupled to the rail body. Some surgical jigs are reversible for performing an osteotomy on either foot or both feet of the subject.

20 Claims, 7 Drawing Sheets

(56) References Cited

U.S. PATENT DOCUMENTS

| | | |
|---|---|---|
| 10,575,862 B2 | 3/2020 | Bays et al. |
| 10,582,936 B1 | 3/2020 | Hissong et al. |
| 10,603,046 B2 | 3/2020 | Dayton et al. |
| 10,849,631 B2 | 12/2020 | Hatch et al. |
| 10,849,663 B2 | 12/2020 | Dayton et al. |
| 10,849,670 B2 | 12/2020 | Santrock et al. |
| 10,874,446 B2 | 12/2020 | Smith et al. |
| 10,888,335 B2 | 1/2021 | Dayton et al. |
| 10,939,939 B1 | 3/2021 | Gil et al. |
| 10,945,764 B2 | 3/2021 | Dayton et al. |
| 11,039,873 B2 | 6/2021 | Santrock et al. |
| 11,076,863 B1 | 8/2021 | Bays et al. |
| 11,116,558 B2 | 9/2021 | Smith et al. |
| 11,147,590 B2 | 10/2021 | Dayton et al. |
| 2016/0015426 A1 | 1/2016 | Dayton |
| 2019/0231394 A1* | 8/2019 | Bechtel ............. A61B 17/7077 |
| 2019/0328435 A1 | 10/2019 | Bays et al. |
| 2020/0015856 A1 | 1/2020 | Treace et al. |
| 2020/0029977 A1 | 1/2020 | Dayton et al. |
| 2020/0155176 A1 | 5/2020 | Bays et al. |
| 2020/0205844 A1 | 7/2020 | Hissong et al. |
| 2020/0253641 A1 | 8/2020 | Treace et al. |
| 2021/0038212 A1 | 2/2021 | May et al. |
| 2021/0093328 A1 | 4/2021 | Dayton et al. |
| 2021/0093365 A1 | 4/2021 | Dayton et al. |
| 2021/0236180 A1 | 8/2021 | DeCarbo et al. |
| 2021/0251659 A1 | 8/2021 | Gil et al. |

* cited by examiner

SURGICAL JIG

REFERENCE TO RELATED APPLICATION

This application claims priority to and the benefit of U.S. Provisional Patent Application No. 63/115,201, filed on Nov. 18, 2020, the contents of which are incorporated herein by reference in their entirety.

FIELD OF THE TECHNOLOGY

The present technology relates generally to surgical instruments, and more particularly to, a surgical jig.

BACKGROUND

Different surgical procedures utilize different instruments and techniques. In an osteotomy for correcting a bunion, for example, the target joint is moved in multiple planes (e.g., three planes) during the surgical procedure. A surgeon performing a conventional osteotomy for correcting a bunion uses two or more surgical instruments to move the target joint in the various planes before the target joint reaches the target position. That is, multiple surgical instruments and/or different surgical instruments are utilized to move the target joint in the various planes during a typical osteotomy, which can be time consuming and/or an inefficient use of surgical instrumentation.

SUMMARY

Surgical jigs for use in performing an osteotomy to correct, for example, a bunion are provided herein. One surgical jig includes a rail body, a contact coupled to the rail body and configured to engage a metatarsal of a subject, and an attachment body coupled to the rail body and configured to engage a cuneiform of the subject.

Another surgical jig includes a rail body, a contact coupled to the rail body and configured to engage a metatarsal of a subject, an arm coupled to the rail body, and an attachment body coupled to the arm and configured to engage a cuneiform of the subject in which the attachment body comprises one or more first apertures and the attachment body is configured to engage the cuneiform of the subject via insertion of one or more first wires through the one or more first apertures and into the cuneiform of the subject. The surgical jig further includes a rail hinge coupling the arm and the rail body and configured to allow the rail body to pivot with respect to the arm when the attachment body is engaged with the cuneiform, a rail adjustment screw coupled to the arm and configured to laterally push the rail body to adjust a lateral position of the metatarsal with respect to the cuneiform, and a rotation guide coupled to the rail body in which the rotation guide comprises one or more notches configured to hold a wire and the rotation guide is configured to facilitate rotation of the metatarsal of the subject and hold, via the wire inserted through and locked in the one or more notches, the metatarsal of the subject in a rotated target position. The surgical jig also includes a distraction body coupled to the rail body in which the distraction body comprises one or more second apertures and the distraction body is configured to engage the metatarsal of the subject via insertion of one or more second wires through the one or more second apertures and into the metatarsal of the subject, and apply at least one of distraction pressure and compaction pressure on the metatarsal when engaged with the metatarsal.

Other embodiments of a surgical jig include a rail body including a first side and a second side opposite the first side, a first contact coupled to the first side of the rail body and configured to engage a left metatarsal of a subject, a second contact coupled to the second side of the rail body and configured to engage a right metatarsal of the subject, an arm detachably and reversibly couplable to the rail body, and an attachment body coupled to the arm and configured to engage a cuneiform of the subject in which the attachment body comprises one or more first apertures and the attachment body is configured to engage the cuneiform of the subject via insertion of one or more first wires through the one or more first apertures and into the cuneiform of the subject. The surgical jig further includes a rail hinge coupling the arm and the rail body and configured to allow the rail body to pivot with respect to the arm when the attachment body is engaged with the cuneiform, a rail adjustment screw coupled to the arm and configured to laterally push the rail body to adjust a lateral position of the left metatarsal or the right metatarsal with respect to the cuneiform, and a rotation guide coupled to the rail body in which the rotation guide comprises one or more notches configured to hold a wire and the rotation guide is configured to facilitate rotation of the left metatarsal or the right metatarsal of the subject and hold, via the wire inserted through and locked in the one or more notches, the left metatarsal or the right metatarsal of the subject in a rotated target position. The surgical jig also includes a distraction body coupled to the rail body in which the distraction body comprises one or more second apertures and the distraction body is configured to engage the left metatarsal or the right metatarsal of the subject via insertion of one or more second wires through the one or more second apertures and into the left metatarsal or the right metatarsal of the subject and apply at least one of distraction pressure and compaction pressure on the left metatarsal or the right metatarsal when engaged with the left metatarsal or the right metatarsal.

BRIEF DESCRIPTION OF THE DRAWINGS

To readily understand the advantages and benefits of the technology, a more particular description of the technology briefly described above will be rendered by reference to specific embodiments that are illustrated in the appended drawings. Understanding that these drawings depict typical embodiments of the technology, and are therefore not to be considered to be limiting of its scope, the technology will be described and explained with additional specificity and detail through the use of the accompanying drawings, in which.

DETAILED DESCRIPTION OF THE DRAWINGS

It should be understood that the language used in the present disclosure has been principally selected for readability and instructional purposes, and not to limit the scope of the subject matter disclosed herein in any manner. Further, reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "having," and variations thereof mean "including, but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise.

In addition, as used herein, the term "set" can mean "one or more," unless expressly specified otherwise. The term "sets" can mean multiples of or a plurality of "one or mores," "ones or more," and/or "ones or mores" consistent with set theory, unless expressly specified otherwise.

Furthermore, the described features, advantages, and characteristics of the embodiments may be combined in any suitable manner. One skilled in the relevant art will recognize that the embodiments may be practiced without one or more of the specific features or advantages of a particular embodiment. In other instances, additional features and advantages may be recognized in certain embodiments that may not be present in all embodiments.

Furthermore, the described features, structures, or characteristics of the various embodiments disclosed herein may be combined in any suitable manner. One skilled in the relevant art will recognize, however, that embodiments may be practiced without one or more of the specific details, or with other methods, components, materials, and so forth. In other instances, well-known structures, and/or materials are not shown or described in detail to avoid obscuring aspects of an embodiment.

Various surgical jigs can include, among other components, an attachment body, a rail body, a distraction body coupled to a set of distraction threads, a rail hinge, a metatarsal contact, an arm, an attachment screw, a rail adjustment screw, and a rotation guide. The various embodiments of a surgical jig include components that are configured to move and/or are capable of moving the metatarsal of a subject (e.g., a patient) in three planes during a surgical procedure, which can allow and/or enable a medical professional (e.g., a surgeon) to perform an osteotomy to correct, for example, a bunion on the subject's metatarsal utilizing a single surgical instrument.

Figure 1A:
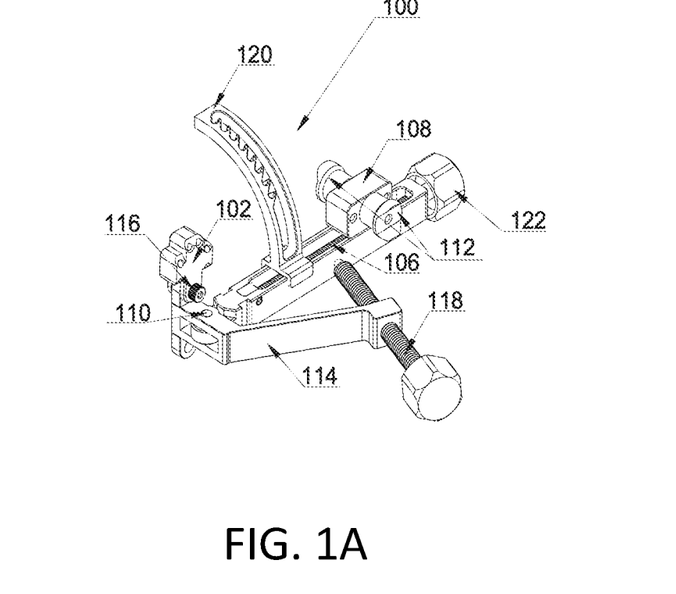
FIG. 1A is a diagram illustrating a non-planar view of one embodiment of a surgical jig.
Figure 1B:
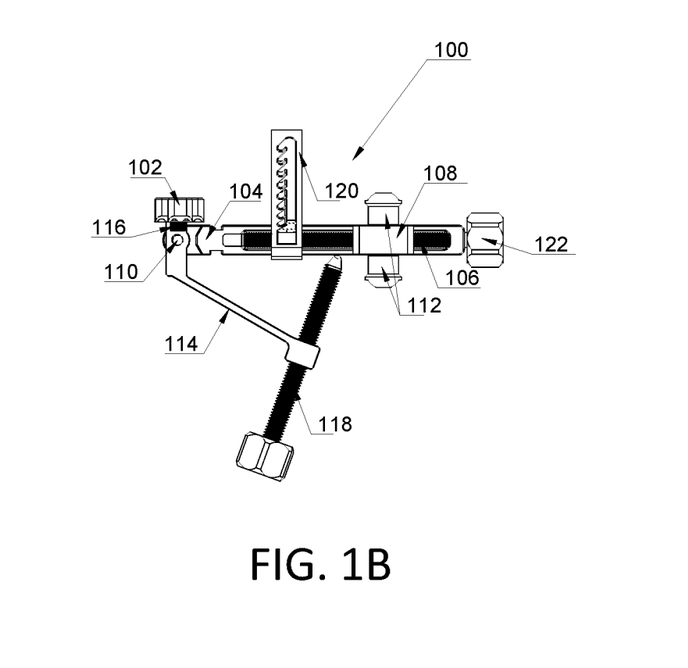
FIG. 1B is a diagram illustrating a top view of the surgical jig illustrated on FIG. 1.

Turning now to the drawings, FIG. 1A is a diagram illustrating a non-planar view of one embodiment of a surgical jig 100 and FIG. 1B is a diagram illustrating a top view of the surgical jig 100. At least in the illustrated embodiment, the surgical jig 100 includes, among other components, an attachment body 102, a rail body 104, a distraction body 108 coupled to a set of distraction threads 106, a rail hinge 110, a metatarsal contact 112, an arm 114, an attachment screw 116, a rail adjustment screw 118, and a rotation guide 120.

The surgical jig 100 may be formed of any suitable material (e.g., a metal, an alloy, a plastic, a composite, and/or a graphite material, etc., among other materials that are possible and contemplated herein). In certain embodiments, the material included in and/or forming the surgical jig 100 is sterilizable.

In certain embodiments, the attachment body 102, rail body 104, set of distraction threads 106, distraction body 108, rail hinge 110, metatarsal contact 112, arm 114, attachment screw 116, rail adjustment screw 118, and rotation guide 120 all include and/or are formed of the same or substantially the same material(s). In other embodiments, at least two of the attachment body 102, rail body 104, set of distraction threads 106, distraction body 108, rail hinge 110, metatarsal contact 112, arm 114, attachment screw 116, rail adjustment screw 118, and rotation guide 120 include and/or are formed of the same or substantially the same material(s). In certain embodiments, the attachment body 102, rail body 104, set of distraction threads 106, distraction body 108, rail hinge 110, metatarsal contact 112, arm 114, attachment screw 116, rail adjustment screw 118, and rotation guide 120 include and/or are formed of different materials or substantially different materials.

In some embodiments, the attachment body 102, rail body 104, set of distraction threads 106, distraction body 108, rail hinge 110, metatarsal contact 112, arm 114, attachment screw 116, rail adjustment screw 118, and rotation guide 120 all include and/or are formed of different materials. In other embodiments, at least two of the attachment body 102, rail body 104, set of distraction threads 106, distraction body 108, rail hinge 110, metatarsal contact 112, arm 114, attachment screw 116, rail adjustment screw 118, and rotation guide 120 include and/or are formed of different materials.

The surgical jig 100 may include any suitable dimensions capable of facilitating its various functions in performing an osteotomy. That is, the surgical jig 100 and/or its various components may include any suitable length, width, height, and/or diameter, etc., among other dimensions that are possible and contemplated herein.

In various embodiments, the attachment body 102 is configured to attach the surgical jig 100 to a cuneiform of a patient. The attachment body 102 includes a set of apertures in which one or more of the apertures are angled apertures and one or more of the apertures are straight apertures. Surgical pins can be inserted through the apertures and into the patient's cuneiform to attach the surgical jig 100 to the cuneiform.

The rail body 104, in certain embodiments, includes a shape configured to run adjacent to a first metatarsal of the patient. Movement of the rail body 104 is controlled by the rail adjustment screw 118 so that the distraction body 108 and/or the metatarsal contact 112 can apply force on the patient's metatarsal to correct its position. The rail body 104 can also act as a housing for the set of distraction threads 106 so that when a knob 122 coupled to the set of distraction threads 106 is turned, the distraction body 108 to moved to compress and compact the patient's cuneiform-metatarsal joint.

The function of the rotation guide 120 may also be dependent on the distraction body 108. Here, as the distraction body 108 moves along the rail body 104, the distraction body 108 provides stability to the rotation guide 120 to hold any rotation created by the rotation guide in a patient's metatarsal. In some embodiments, the rail body 104 includes a set of notches that allow for the removal of the rotation guide 120.

The knob 122, the set of distraction threads 106, and the distraction body 108 are configured to cooperatively function to compress or distract the cuneiform-metatarsal joint of a patient. The rotation of the knob 122 rotates the set of distraction threads 106, which are coupled to the distraction body 108, and moves the distraction body 108 along the rail body 104. When pins are placed through the distraction body 108 and into the patient's metatarsal, movement of the distraction body 108 along the rail body 104 will result in the joint being compressed or distracted.

As shown, the distraction body 108 is threaded onto the set of distraction threads 106 and the set of distraction threads 106 use the length of the rail body 104 as a path to move along when the knob 122 is turned. A set of holes through the distraction body 108 allow for a set of pins to be placed into the patient's metatarsal for compaction and/or distraction.

The rail hinge 110 may include any suitable hinging mechanism that can allow the rail body 104 to pivot laterally. In certain embodiments, the rail hinge 110 includes a bolt attaching the rail body 104 and the arm 114, which can allow the arm 114 to rotate and/or pivot freely. In some embodiments, the arm 114 can be removed so that the surgical jig 100 can be reassembled into a right or left configuration for performing a procedure on a right foot or a left foot, as discussed in greater detail below with reference to FIG. 2.

A metatarsal contact 112 includes a rotating piece and/or mechanism with a shape configured to match the curvature of a patient's metatarsal. The curvature is configured to prevent slipping when correcting the position and/or angle of the patient's metatarsal. The rotation allows the curvature of the metatarsal contact 112 to wrap around at least a portion of the target bone for various placements of the surgical jig 100.

The arm 114 is configured to hold the rail adjustment screw 118 so that the rail adjustment screw 118 can push the rail body 104 when the rail adjustment screw 118 is rotated. The arm 114 is a structural piece that is coupled to the attachment body 102, rail body 104, and rail adjustment screw 118. The arm 114, in some embodiments, is further configured for use in switching between the left and right configurations illustrated in FIG. 2.

The attachment screw 116 is configured to lock the rotation of the arm 114 around the attachment body 102. The attachment screw 116 may include any suitable mechanism capable of locking the rotation of the arm 114 around the attachment body 102.

The rail adjustment screw 118 is configured to apply a force to the rail body 104 to push/move the rail body 104 laterally. Laterally pushing and/or moving the rail body 104, in turn, causes the rail body 104 to laterally push and/or move the patient's metatarsal.

The rotation guide 120 is configured to hold any amount of rotation applied to the patient's metatarsal. The rotation guide 120, in various embodiments, includes a set of slots or notches through which a wire may be placed therethrough. The wire can be rotated and locked into the desired slot to hold a target amount of rotation applied to the patient's metatarsal. Alternatively, a wire can be placed through a sliding construct on the rotation guide 120 and the patient's metatarsal can be locked into a target rotated position when the wire is at its desired rotated position.

Figure 2:
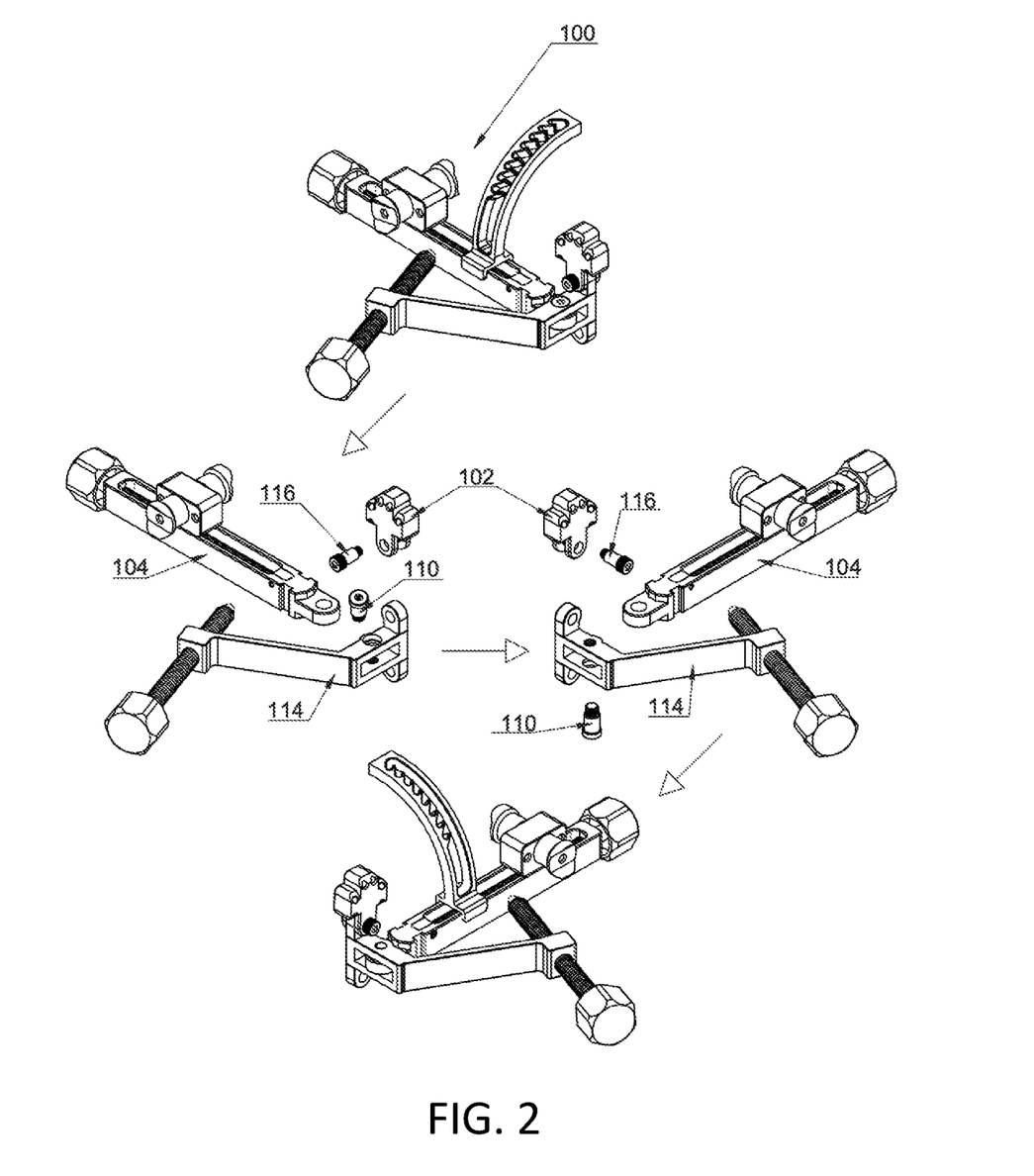
FIG. 2 is a diagram illustrating one embodiment of a surgical jig that is adjustable for performing an osteotomy on a left foot and/or a right foot.

Referring to FIG. 2, FIG. 2 is a diagram illustrating an embodiment of an adjustable surgical jig 100. At least in the illustrated embodiment, the surgical jig 100 is configured for use in performing an osteotomy on a left foot and/or a right foot of a patient.

The surgical jig 100 can be adjusted by removing the rail screw 110 and the attachment screw 116 so that the orientation of the arm 114 can be changed (e.g., turned over) to the desired orientation. In this embodiment, a metatarsal contact 112 is included on both sides of the distraction body 108. Here, a single surgical jig 100 can be utilized to perform an osteotomy on both feet of a patient.

Figure 3:
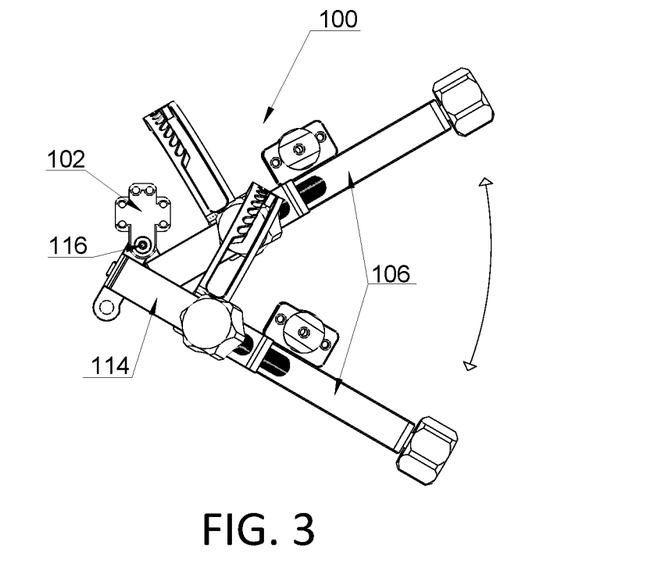
FIG. 3 is a diagram illustrating an embodiment of a surgical jig configured to vertically adjust.

FIG. 3 is a diagram illustrating an embodiment of a surgical jig 100 configured to adjust vertically (e.g., from the cuneiform). The rotation at the junction of the attachment body 102 and the arm 114 allows and/or enables the surgical jig 100 to be vertically positioned so that the patient's metatarsal rests in the curvature and/or groove of the metatarsal contact 112. The rotation created at the junction of the attachment body 102 and the arm 114 can be locked by tightening the attachment screw 116.

Figure 4:
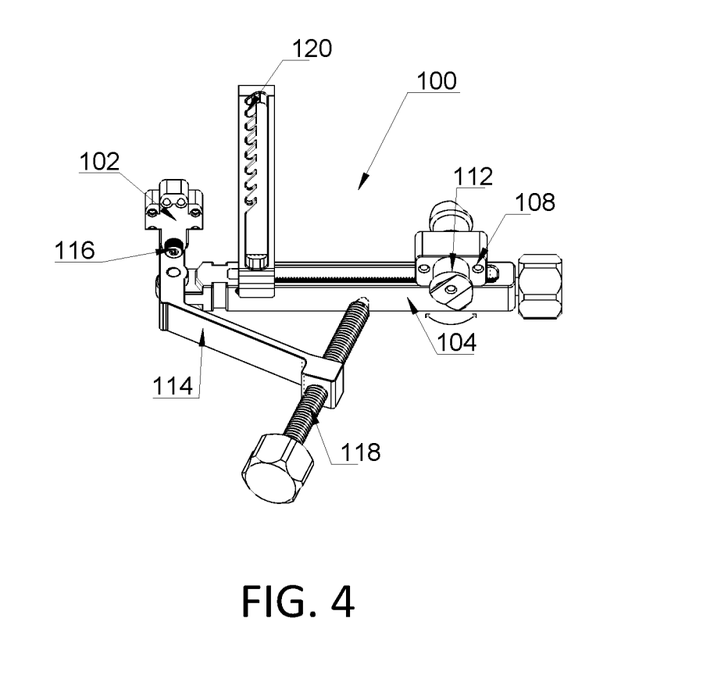
FIG. 4 is a diagram illustrating one embodiment of a surgical jig including a rotating metatarsal contact.

FIG. 4 is a diagram illustrating one embodiment of a surgical jig including a rotatable metatarsal contact 112. In various embodiments, the metatarsal contact 112, in addition to the positional function of the metatarsal contact 112 discussed above, is configured to freely rotate. Rotating the metatarsal contact 112 can allow/enable the best and/or proper fitment of the metatarsal contact 112 with the patient's metatarsal.

Figure 5A:
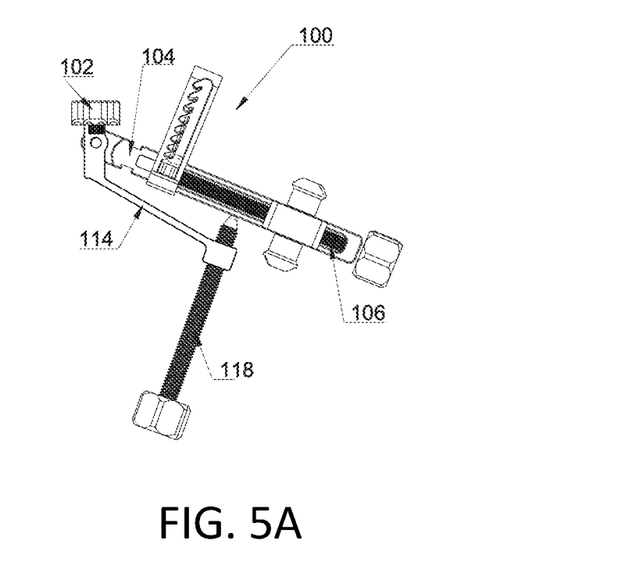
FIG. 5A is a diagram illustrating a first position of an embodiment of a surgical jig configured to laterally move a metatarsal.
Figure 5B:
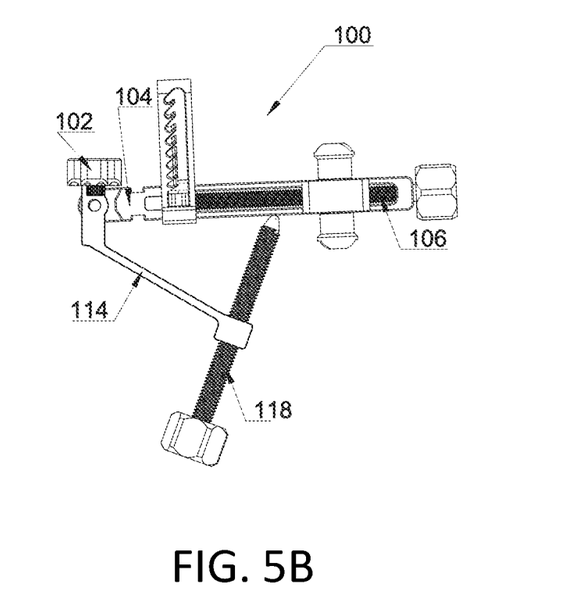
FIG. 5B is a diagram illustrating the surgical jig illustrated in FIG. 5A moved laterally to a second position.

FIGS. 5A and 5B are diagram illustrating an embodiment of the surgical jig 100 configured to laterally move a patient's metatarsal (e.g., adjust the intermetatarsal (IM) angle) between various positions. Here, the attachment body 102 is fixed and/or attached to the patient's cuneiform. The angle of the patient's metatarsal can be corrected by turning the rail adjustment screw 118. The rail adjustment screw 118 applies force to and pushes the rail body 104 from a first position (see, e.g., FIG. 5A) to a second position (see, e.g., FIG. 5B), which in turn can cause the patient's metatarsal to change positions because the patient's metatarsal is in contact with the moving rail body 104 via the metatarsal contact 112.

Figure 6A:
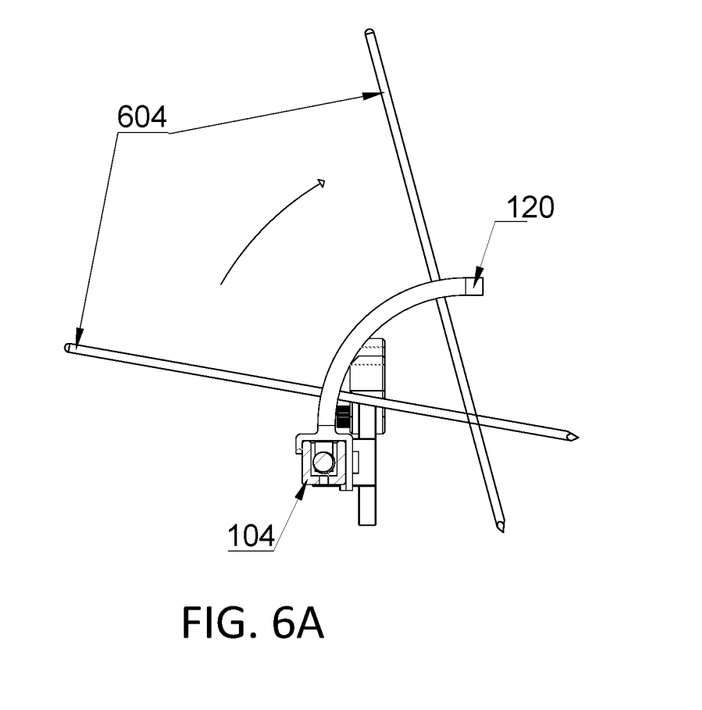
FIG. 6A is a diagram illustrating one embodiment of a surgical jig configured to rotate a metatarsal.
Figure 6B:
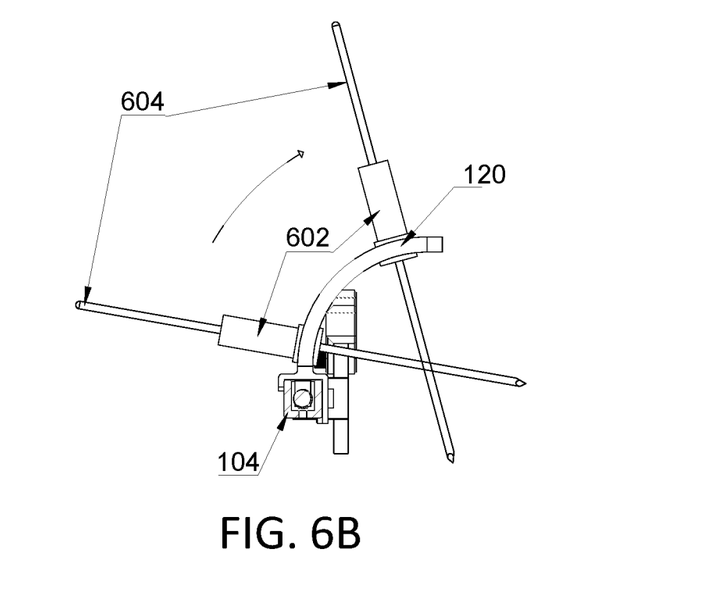
FIG. 6B is a diagram illustrating the surgical jig illustrated in FIG. 6A including a locking mechanism for at least temporarily locking a rotated position of the metatarsal.

FIG. 6A is a diagram illustrating one embodiment of a surgical jig 100 including a set of wires 604 configured to rotate a patient's metatarsal. Further, FIG. 6B is a diagram illustrating a surgical jig 100 including a set of locking mechanisms 602 for at least temporarily locking a rotated position of the patient's metatarsal.

A wire 604 or other suitable type of lever is placed through a slot in the rotation guide 120 and into the patient's metatarsal. The wire 604 can then be used to rotate the patient's metatarsal to a target rotational position.

The rotation of the patient's metatarsal can then be locked into place (e.g., into one or the slots) via coupling each locking mechanism 602 to the rotation guide 120 and/or a wire 604. At least in the illustrated embodiment, the set of locking mechanisms 602 includes two locking mechanisms 602 in which a locking mechanism 602 is coupled to the rotation guide 120 and/or a respective wire 604.

Figure 7A:
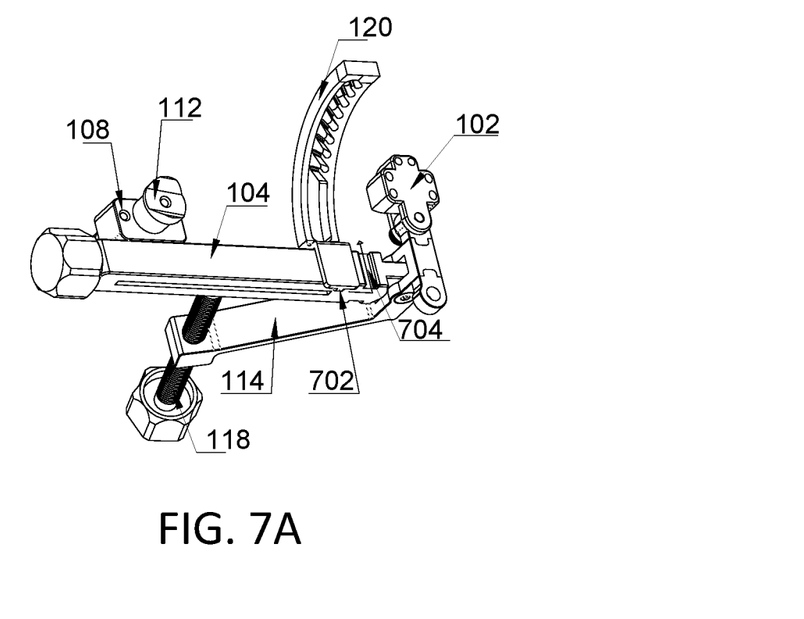
FIGS. 7A and 7B are diagram illustrating an embodiment of removal of a rotation guide from a surgical jig.
Figure 7B:
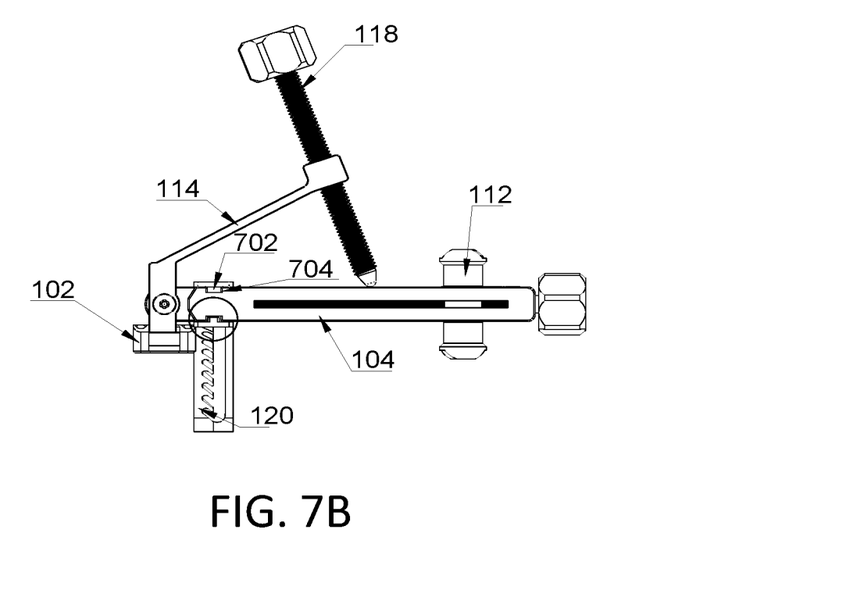

FIGS. 7A and 7B are diagram illustrating an embodiment of removal of a rotation guide 120 from a surgical jig 100 including an aperture for inserting a surgical pin to further at least temporarily lock the rotated position of the patient's metatarsal. After the locking mechanism 602, wire 604, and rotation guide 120 rotate the patient's metatarsal to the target rotational position, a set of pins are placed through a set of apertures formed in the distraction body 108 to further lock the patient's metatarsal in its rotational position. The wire 604 used in the rotation guide 120 can then be removed from the rotation guide 120 and the set of pins through the distraction body 108 can hold the patient's metatarsal in place. The rotation guide 120 can then be removed or left in place.

To remove rotation guide 120, a tab 702 on the bottom of the rotation guide 120 can be aligned with a notch 704 in the rail body 104, as shown in FIG. 7A. Once the tab 702 and the notch 704 are aligned, the rotation guide 120 can be removed by pulling up on the rotation guide 120.

Figure 8A:
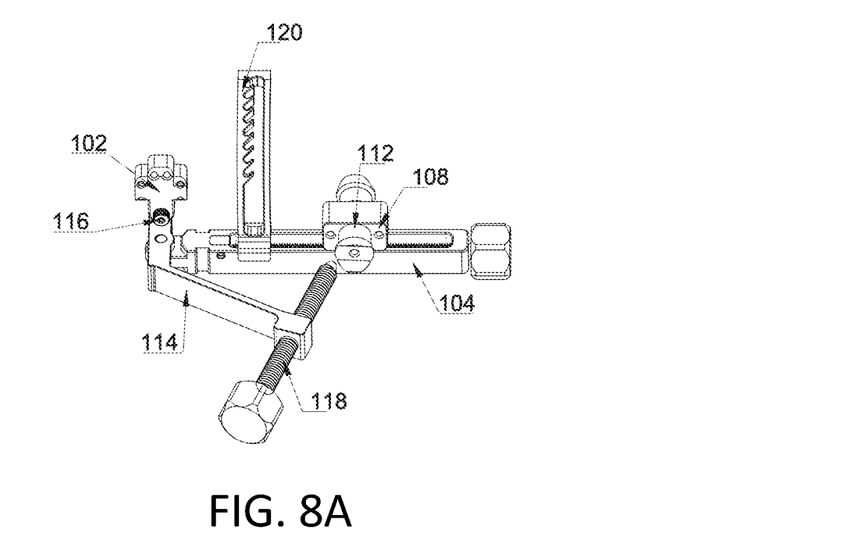
FIGS. 8A and 8B are diagrams illustrating one embodiment of a surgical jig including a distraction body configured to compress and/or distract a cuneiform-metatarsal joint.
Figure 8B:
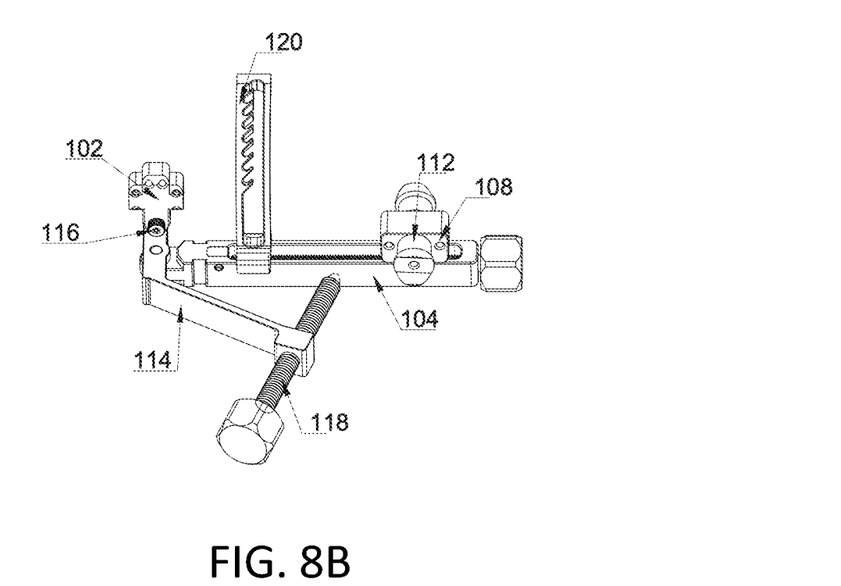

FIGS. 8A and 8B are diagrams illustrating one embodiment of a surgical jig 100 including a distraction body 108 configured to compress and/or distract the cuneiform-metatarsal joint of a patient. During operation, the knob 122 coupled to the set of distraction threads 106 can be rotated to move the distraction body 108 along the rail body 104, which acts as a rail and/or path. When one or more pins are placed through one or more apertures formed on the distraction body 108 and into a patient's metatarsal, the turning of the knob 122 (and the set of distraction threads 106) causes the distraction body 108 to move, which causes compression or distraction of the patient's cuneiform-metatarsal joint depending on the direction that the distraction body 108 is moving. That is, the patient's cuneiform-metatarsal joint is compressed when the distraction body 108 is moved along the rail body 104 toward the rotation guide 120 (see, e.g., FIG. 8A) and distracted when the distraction body 108 is moved along the rail body 104 away from the rotation guide 120 (see, e.g., FIG. 8B).

The invention claimed is:

1. An apparatus, comprising:
a rail body comprising a knob and a set of threads coupled to the knob, wherein the set of threads is housed within the rail body;
a distraction body coupled to the set of threads of the rail body, wherein:
the distraction body comprises:
a contact coupled to the distraction body and configured to engage a metatarsal of a subject, and
at least one aperture for receiving a second wire to engage the metatarsal of the subject, and
the distraction body is configured to move along the rail body to apply at least one of distraction pressure and compaction pressure on the metatarsal in response to the knob and the set of threads being turned relative to the rail body when the distraction body is engaged with the metatarsal;
an attachment body coupled to the rail body and configured to engage a cuneiform of the subject, wherein the attachment body includes at least one aperture for receiving a first wire to engage the cuneiform of the subject;
an arm coupled to the rail body and the attachment body;
a rail hinge coupling the arm to the rail body and configured to allow the rail body to pivot with respect to the arm when the attachment body is engaged with the cuneiform; and
a rail adjustment screw coupled to the arm and configured to laterally push the rail body away from the arm to adjust a lateral position of the metatarsal with respect to the cuneiform.

2. The apparatus of claim 1, wherein:
the attachment body is configured to engage the cuneiform of the subject via insertion of one or more wires through the at least one aperture and into the cuneiform of the subject.

3. The apparatus of claim 1, wherein the apparatus is configured to facilitate performing an osteotomy on the subject.

4. The apparatus of claim 1, wherein the apparatus of configured to facilitate performing an osteotomy to correct a bunion of the subject.

5. The apparatus of claim 1, wherein:
the attachment body is coupled to the rail body via the arm.

6. The apparatus of claim 5, wherein:
the arm and the attachment body are detachably coupled to the rail body via the rail hinge; and
the detachable arm and the attachment body are configured to enable the apparatus to be reversable to perform an osteotomy to correct a bunion on either foot of the subject.

7. The apparatus of claim 1, further comprising:
a rotation guide coupled to the rail body and configured to facilitate rotation of the metatarsal of the subject.

8. The apparatus of claim 7, wherein:
the arm and the attachment body are detachably coupled to the rail body via the rail hinge;
the rotation guide is detachably coupled to the rail body; and
the detachable arm with the attachment body and the detachable rotation guide are configured to enable the apparatus to be reversable to perform an osteotomy to correct a bunion on either foot of the subject.

9. The apparatus of claim 8, wherein:
the contact is a first contact; and
the apparatus further comprises a second contact positioned on a side of the distraction body opposite the first contact.

10. The apparatus of claim 9, wherein:
the distraction body is configured to engage the metatarsal of the subject via insertion of one or more wires through the at least one aperture and into the metatarsal of the subject.

11. The apparatus of claim 7, wherein:
the rotation guide comprises one or more notches configured to hold a wire; and
the rotation guide is further configured to:
hold, via the wire inserted through and locked in the one or more notches, the metatarsal of the subject in a rotated target position.

12. The apparatus of claim 11, wherein the rotation guide is detachably coupled to the rail and is configured to enable the apparatus to be reversable to perform an osteotomy to correct a bunion on either foot of the subject.

13. The apparatus of claim 1, wherein:
the contact is a first contact;
the apparatus further comprises a second contact positioned on a side of the distraction body opposite the first contact; and
the first contact and the second contact enable the apparatus to be reversable to perform an osteotomy to correct a bunion on either foot of the subject.

14. The apparatus of claim 12, wherein:
the contact is a first contact; and
the apparatus further comprises a second contact positioned on a side of the distraction body opposite the first contact.

15. The apparatus of claim 11, wherein the distraction body is further configured to:
engage the metatarsal of the subject via insertion of one or more wires through the at least one aperture and into the metatarsal of the subject.

16. The apparatus of claim 1, wherein the distraction body is further configured to:
engage the metatarsal of the subject via insertion of one or more wires through the at least one aperture and into the metatarsal of the subject.

17. The apparatus of claim 15, wherein:
the contact is a first contact;
the apparatus further comprises a second contact positioned on a side of the distraction body opposite the first contact; and
the first contact and the second contact enable the apparatus to be reversable to perform an osteotomy to correct a bunion on either foot of the subject.

18. The apparatus of claim 17, wherein the rotation guide is detachably coupled to the rail to further enable the apparatus to be reversable to perform the osteotomy to correct the bunion on either foot of the subject.

19. An apparatus, comprising:
a rail body including a knob and a set of threads coupled to the knob;
a distraction body coupled to the set of threads of the rail body, wherein:
  the distraction body comprises:
    a contact coupled to the distraction body and configured to engage a metatarsal of a subject, and
    one or more second apertures, and
  the distraction body is configured to:
    engage the metatarsal of the subject via insertion of one or more second wires through the one or more second apertures and into the metatarsal of the subject, and
    move along the rail body to apply at least one of distraction pressure and compaction pressure on the metatarsal in response to the knob and the set of threads being turned relative to the rail body when the distraction body is engaged with the metatarsal;
an arm coupled to the rail body;
an attachment body coupled to the arm and configured to engage a cuneiform of the subject, wherein:
  the attachment body comprises one or more first apertures, and
  the attachment body is configured to engage the cuneiform of the subject via insertion of one or more first wires through the one or more first apertures and into the cuneiform of the subject;
a rail hinge coupling the arm and the rail body and configured to allow the rail body to pivot with respect to the arm when the attachment body is engaged with the cuneiform;
a rail adjustment screw coupled to the arm and configured to laterally push the rail body away from the arm to adjust a lateral position of the metatarsal with respect to the cuneiform;
a rotation guide coupled to the rail body, wherein:
  the rotation guide comprises one or more notches configured to hold a wire, and
  the rotation guide is configured to:
    facilitate rotation of the metatarsal of the subject, and
    hold, via the wire inserted through and locked in the one or more notches, the metatarsal of the subject in a rotated target position.

20. An apparatus, comprising:
a rail body including a knob and a set of threads coupled to the knob;
a distraction body coupled to the set of threads of the rail body, wherein:
  the distraction body comprises:
    a first side and a second side opposite the first side,
    a first contact coupled to the first side of the distraction body and configured to engage a left metatarsal of a subject,
    a second contact coupled to the second side of the distraction body and configured to engage a right metatarsal of the subject,
    one or more second apertures, and
  the distraction body is configured to:
    engage the left metatarsal or the right metatarsal of the subject via insertion of one or more second wires through the one or more second apertures and into the left metatarsal or the right metatarsal of the subject, and
    move along the rail body to apply at least one of distraction pressure and compaction pressure on the left metatarsal or the right metatarsal in response to the knob and the set of threads being turned relative to the rail body when the distraction body is engaged with the left metatarsal or the right metatarsal;
an arm detachably and reversibly couplable to the rail body;
an attachment body coupled to the arm and configured to engage a cuneiform of the subject, wherein:
  the attachment body comprises one or more first apertures, and
  the attachment body is configured to engage the cuneiform of the subject via insertion of one or more first wires through the one or more first apertures and into the cuneiform of the subject;
a rail hinge coupling the arm and the rail body and configured to allow the rail body to pivot with respect to the arm when the attachment body is engaged with the cuneiform;
a rail adjustment screw coupled to the arm and configured to laterally push the rail body away from the arm to adjust a lateral position of the left metatarsal or the right metatarsal with respect to the cuneiform; and
a rotation guide coupled to the rail body, wherein:
  the rotation guide comprises one or more notches configured to hold a wire, and the rotation guide is configured to:
    facilitate rotation of the left metatarsal or the right metatarsal of the subject, and
    hold, via the wire inserted through and locked in the one or more notches, the left metatarsal or the right metatarsal of the subject in a rotated target position.

* * * * *